US012765779B2

(12) United States Patent
Yao et al.

(10) Patent No.: US 12,765,779 B2
(45) Date of Patent: Oct. 20, 2026

(54) WEARABLE DEVICE AND TEMPERATURE MEASUREMENT METHOD

(71) Applicant: HONOR DEVICE CO., LTD., Shenzhen (CN)

(72) Inventors: Chao Yao, Shenzhen (CN); Chenlong Li, Shenzhen (CN); Ning Zhang, Shenzhen (CN)

(73) Assignee: HONOR DEVICE CO., LTD., Shenzhen (CN)

( * ) Notice: Subject to any disclaimer, the term of this patent is extended or adjusted under 35 U.S.C. 154(b) by 578 days.

(21) Appl. No.: 18/025,168

(22) PCT Filed: Sep. 2, 2022

(86) PCT No.: PCT/CN2022/116906

§ 371 (c)(1),
(2) Date: Mar. 7, 2023

(87) PCT Pub. No.: WO2023/116049

PCT Pub. Date: Jun. 29, 2023

(65) Prior Publication Data

US 2024/0172944 A1 May 30, 2024

(30) Foreign Application Priority Data

Dec. 21, 2021 (CN) ......................... 202111573033.1

(51) Int. Cl.
*A61B 5/01* (2006.01)
*A61B 5/00* (2006.01)

(52) U.S. Cl.
CPC .............. *A61B 5/01* (2013.01); *A61B 5/6817* (2013.01); *A61B 5/6843* (2013.01); *A61B 5/7285* (2013.01); *A61B 5/746* (2013.01)

(58) Field of Classification Search
CPC ....... A61B 5/01; A61B 5/6817; A61B 5/6843; A61B 5/7285; A61B 5/746; A61B 5/0008; A61B 2562/0271
See application file for complete search history.

(56) References Cited

U.S. PATENT DOCUMENTS 6,090,050 A 7/2000 Constantinides
2014/0266694 A1* 9/2014 McCluskey ........ G08B 21/0453 340/539.12
(Continued)

FOREIGN PATENT DOCUMENTS

CN 202842494 U 4/2013
CN 104083152 A 10/2014
(Continued)

*Primary Examiner* — Alex M Valvis
(74) *Attorney, Agent, or Firm* — WOMBLE BOND DICKINSON (US) LLP

(57) ABSTRACT

This application relates to the field of temperature measurement technologies, and provides a wearable device and a temperature measurement method. The wearable device includes a first sensing member, a second sensing member, and a processor. When the wearable device is close to a biological body, the first sensing member forms equivalent capacitance with the biological body, and the first sensing member receives heat of the biological body. The second sensing member is configured to measure temperature of the first sensing member as an initial temperature. The processor is configured to read a capacitance value of the equivalent capacitance and determine a contact state between the first sensing member and the biological body according to the capacitance value. The processor is configured to determine whether to match a corresponding temperature compensation value to the initial temperature according to the contact state.

20 Claims, 7 Drawing Sheets

(56) References Cited

U.S. PATENT DOCUMENTS

| | | | | |
|---|---|---|---|---|
| 2016/0038055 | A1* | 2/2016 | Wheeler | A61B 5/7225 600/301 |
| 2016/0317781 | A1* | 11/2016 | Proud | A61B 5/01 |
| 2017/0049335 | A1 | 2/2017 | Duddy | |
| 2018/0039233 | A1 | 2/2018 | Shim et al. | |
| 2019/0082968 | A1* | 3/2019 | Karnik | A61B 5/01 |
| 2019/0282098 | A1* | 9/2019 | Proud | A61B 5/0022 |
| 2020/0085310 | A1* | 3/2020 | Zahner | G04G 17/00 |
| 2020/0314527 | A1 | 10/2020 | Guo et al. | |
| 2022/0000368 | A1 | 1/2022 | Meisal | |

FOREIGN PATENT DOCUMENTS

| | | | | | |
|---|---|---|---|---|---|
| CN | 104378707 | A | | 2/2015 | |
| CN | 104633860 | A | | 5/2015 | |
| CN | 108810788 | A | | 11/2018 | |
| CN | 110750131 | A | | 2/2020 | |
| CN | 111366175 | A | * | 7/2020 | G01K 13/223 |
| CN | 111417042 | A | | 7/2020 | |
| CN | 111565342 | A | | 8/2020 | |
| CN | 111854966 | A | * | 10/2020 | G01J 5/068 |
| CN | 213043825 | U | | 4/2021 | |
| CN | 113164069 | A | | 7/2021 | |
| JP | 2018013366 | A | | 1/2018 | |
| TW | M506284 | U | | 8/2015 | |
| WO | WO-2016039795 | A1 | * | 3/2016 | A61B 5/6817 |
| WO | 2017096978 | A1 | | 6/2017 | |
| WO | WO-2018047046 | A1 | * | 3/2018 | A61B 5/113 |

* cited by examiner

WEARABLE DEVICE AND TEMPERATURE MEASUREMENT METHOD

CROSS-REFERENCE TO RELATED APPLICATIONS

This application is a national stage of International Application No. PCT/CN2022/116906 filed on Sep. 2, 2022, which claims priority to Chinese Patent Application No. 202111573033.1 filed on Dec. 21, 2021. The disclosures of both of the aforementioned application are hereby incorporated by reference in their entireties.

TECHNICAL FIELD

This application relates to the field of temperature measurement technologies, and in particular, to a wearable device capable of measuring user temperature and a temperature measurement method applied to such wearable device.

BACKGROUND

As one of vital signs of a human body, body temperature reflects a health condition of the human body to some extent. Therefore, body temperature measurement results, especially long-time continuous body temperature measurement results, have practical significance for menstrual cycle management, biological rhythm regulation, chronic disease management, and the like.

At present, people usually choose the armpit, forehead, chest, or other parts for temperature measurement to obtain a body temperature measurement result. However, measurement accuracy of such body temperature measurement manner is unable to satisfy user requirements, resulting in poor user experience.

SUMMARY

In view of this, embodiments of this application provide a wearable device and a temperature measurement method for measuring temperature of a biological body, with relatively high temperature measurement accuracy.

According to a first aspect of embodiments of this application, a wearable device is provided, configured to measure temperature of a biological body. The wearable device includes a first sensing member, a second sensing member, and a processor. The first sensing member is configured to obtain capacitance. The second sensing member is configured to measure temperature of the first sensing member as an initial temperature. The processor is electrically connected to the first sensing member, and configured to read the capacitance value and determine a contact state of the wearable device according to the capacitance value. The processor is further electrically connected to the second sensing member, and configured to read the initial temperature obtained by the second sensing member and, according to the contact state between the first sensing member and the biological body, directly take the initial temperature as a measured temperature, or match a corresponding temperature compensation value to the initial temperature and take a sum of the initial temperature and the temperature compensation value as a measured temperature.

In the solution provided in embodiments of this application, the first sensing member forms equivalent capacitance with epidermis of the biological body, so as to characterize a contact state between the wearable device and the biological body by using a capacitance value of the equivalent capacitance: the first sensing member receives heat of the biological body and the second sensing member measures the temperature of the first sensing member, so as to preliminarily measure the temperature of the biological body: and the processor is electrically connected to the first sensing member and the second sensing member, so as to take the currently obtained initial temperature as the measured temperature or match the corresponding temperature compensation value to the current initial temperature, according to the contact state. In this way, compared with an existing contact-type temperature measurement apparatus, the wearable device provided in embodiments of this application further corrects the measured temperature by examining the contact state between the wearable device and the epidermis of the biological body, thereby improving data accuracy.

In a possible implementation, the wearable device includes a housing, and the housing is provided with an opening. The first sensing member is partly accommodated in the opening so that the first sensing member protrudes from a surface of the housing through the opening.

In the solution provided in embodiments of this application, an opening is provided to accommodate the first sensing member, which not only allows mounting of the first sensing member but also allows the first sensing member to protrude from the housing so as to contact epidermis of a user conveniently and absorb heat of the user.

In a possible implementation, the second sensing member is fitted onto the first sensing member.

In a possible implementation, the first sensing member covers the second sensing member, and an insulating and thermally conductive material is filled between the first sensing member and the second sensing member.

In the solution provided in embodiments of this application, the second sensing member is fitted onto the first sensing member, or an insulating and thermally conductive material is filled between the first sensing member and the second sensing member, reducing unnecessary heat loss and environment interference, thereby improving accuracy of measuring temperature of the first sensing member by the second sensing member.

In a possible implementation, the first sensing member is provided with an accommodating hole, and the second sensing member is accommodated in the accommodating hole.

In the solution provided in embodiments of this application, the second sensing member is accommodated in the accommodating hole formed in the first sensing member, so that the first sensing member better covers the second sensing member, improving accuracy of measuring temperature of the first sensing member by the second sensing member.

In a possible implementation, the wearable device includes a housing. The housing includes an outer surface and an inner surface. The outer surface is provided with the first sensing member, and the inner surface is provided with the second sensing member. In this way, heat of the first sensing member is conducted to the housing, and the second sensing member obtains the temperature of the first sensing member by measuring temperature of the housing.

In the solution provided in embodiments of this application, an insulating and thermally conductive housing is disposed between the first sensing member and the second sensing member, so that the first sensing member can be directly disposed on a surface of the wearable device to contact the epidermis of the user.

In a possible implementation, the first sensing member has electric conductivity and thermal conductivity.

In the solution provided in embodiments of this application, the first sensing member is made of a material having electric conductivity and thermal conductivity, so that the first sensing member can quickly receive heat of the biological body to reach a thermal equilibrium state, while forming equivalent capacitance with the epidermis of the biological body, thereby reducing time for reading the initial temperature.

In a possible implementation, the first sensing member is made of a metal material. The second sensing member is a temperature sensor.

In the solution provided in embodiments of this application, the first sensing member is made of metal having good electric conductivity and thermal conductivity, and a temperature sensor is used as the second sensing member. Such solution is easy to implement, and allows the processor to quickly read the temperature.

In a possible implementation, when the capacitance value is greater than or equal to a first capacitance threshold, the contact state is determined to be a touch state, and the initial temperature is taken as the measured temperature of the biological body.

In the solution provided in embodiments of this application, the contact state is determined according to the capacitance value of the equivalent capacitance formed between the first sensing member and the epidermis of the biological body. When the processor determines that the first sensing member is in the touch state with the biological body, meaning that the first sensing member is in contact with the biological body, the processor considers that the currently obtained initial temperature is reliable data which can represent the temperature of the biological body.

In a possible implementation, when the contact state is the touch state, the second sensing member is further controlled to start temperature measurement, and read the initial temperature when the first sensing member reaches a thermal equilibrium state after a preset time.

In the solution provided in embodiments of this application, the initial temperature is read only when the first sensing member and the epidermis of the biological body reach the touch state and the first sensing member reaches the thermal equilibrium state, further improving temperature measurement accuracy of the wearable device.

In a possible implementation, when the capacitance value is less than the first capacitance threshold and greater than or equal to a second capacitance threshold, the contact state is determined to be a proximity state, the corresponding temperature compensation value is matched to the initial temperature, and the sum of the initial temperature and the temperature compensation value is taken as the measured temperature.

In the solution provided in embodiments of this application, when the contact state is the proximity state, meaning that the first sensing member is apart from the epidermis of the biological body by an acceptable distance, the processor matches the corresponding temperature compensation value to the initial temperature, and takes the sum of the initial temperature and the temperature compensation value as the measured temperature of the biological body. In this way, the measured temperature of the biological body can be corrected, improving data accuracy.

In a possible implementation, a distance value between the first sensing member and the biological body is positively correlated with the temperature compensation value. A relationship between the temperature compensation value and the capacitance value satisfies a preset function, and the processor calculates the temperature compensation value based on the preset function and the obtained capacitance value. The capacitance value is negatively correlated with the temperature compensation value.

In a possible implementation, when the capacitance value is less than the second capacitance threshold, the first sensing member and the biological body are determined to be in a hovering state. The wearable device further includes an alert module, and when the first sensing member and the biological body are determined to be in the hovering state, the alert module is configured to output alert information under control of the processor.

In the solution provided in embodiments of this application, when the contact state is determined to be the hovering state, meaning that the first sensing member is apart from the epidermis of the biological body by an unacceptable distance, the alert module is further controlled to alert a user to tighten the wearable device, so that the contact state between the first sensing member and the biological body is restored to the touch state or the proximity state, thus effectively improving temperature measurement accuracy.

In a possible implementation, the wearable device further includes an analog to digital converter. The analog to digital converter has one end connected to the first sensing member and another end connected to the processor. The analog to digital converter is configured to convert the capacitance value into a digital quantity.

In the solution provided in embodiments of this application, the analog to digital converter is provided to convert the capacitance value into a digital quantity, thereby characterizing the contact state by using the digital quantity.

In a possible implementation, a functional relationship between the temperature compensation value and the digital quantity is:

$$T_{com}=-0.00004(a-5500)^2+0.0995(a-5500)-61.303,$$

where $T_{com}$ represents the temperature compensation value and a represents the digital quantity.

In the solution provided in embodiments of this application, the temperature compensation value is calculated based on the function between the temperature compensation value and the digital quantity.

According to a second aspect of embodiments of this application, a temperature measurement method is further provided, which is applied to a wearable device and can effectively improve temperature measurement accuracy of the wearable device.

In a possible implementation, the wearable device includes a first sensing member and a second sensing member. The first sensing member is configured to obtain a capacitance value, and the second sensing member is configured to measure temperature of the first sensing member as an initial temperature. The temperature measurement method includes:

reading a capacitance value of the first sensing member to determine a contact state of the wearable device: and according to the contact state, taking the initial temperature as a measured temperature, or matching a corresponding temperature compensation value to the initial temperature and taking a sum of the initial temperature and the temperature compensation value as a measured temperature.

In a possible implementation, when the capacitance value is greater than or equal to a first capacitance threshold, the contact state is determined to be a touch state, and the initial temperature is taken as the measured temperature.

In a possible implementation, when the capacitance value is less than the first capacitance threshold and greater than or equal to a second capacitance threshold, the contact state is determined to be a proximity state, the corresponding temperature compensation value is matched to the initial temperature, and the sum of the initial temperature and the temperature compensation value is taken as the measured temperature.

In a possible implementation, when the capacitance value is less than the second capacitance threshold, the contact state is determined to be a hovering state.

In a possible implementation, the wearable device further includes an alert module, and when the contact state is determined to be the hovering state, controls the alert module to output alert information.

In a possible implementation, the wearable device further includes an analog to digital converter, the analog to digital converter has one end connected to the first sensing member and another end connected to the processor, and the analog to digital converter is configured to convert the capacitance value into a digital quantity, where a functional relationship between the temperature compensation value and the digital quantity is:

$$T_{com}=-0.00004(a-5500)^2+0.0995(a-5500)-61.303,$$

where $T_{com}$ represents the temperature compensation value and a represents the digital quantity.

BRIEF DESCRIPTION OF DRAWINGS

In order to describe the technical solutions in the embodiments of this application more clearly, the following briefly describes the accompanying drawings in the embodiments. It should be understood that, the accompanying drawings below only show some embodiments of this application, and thus should not be considered as limitations on the scope. Persons of ordinary skill in the art may still derive other related drawings from the accompanying drawings without creative efforts.

Figure 1:
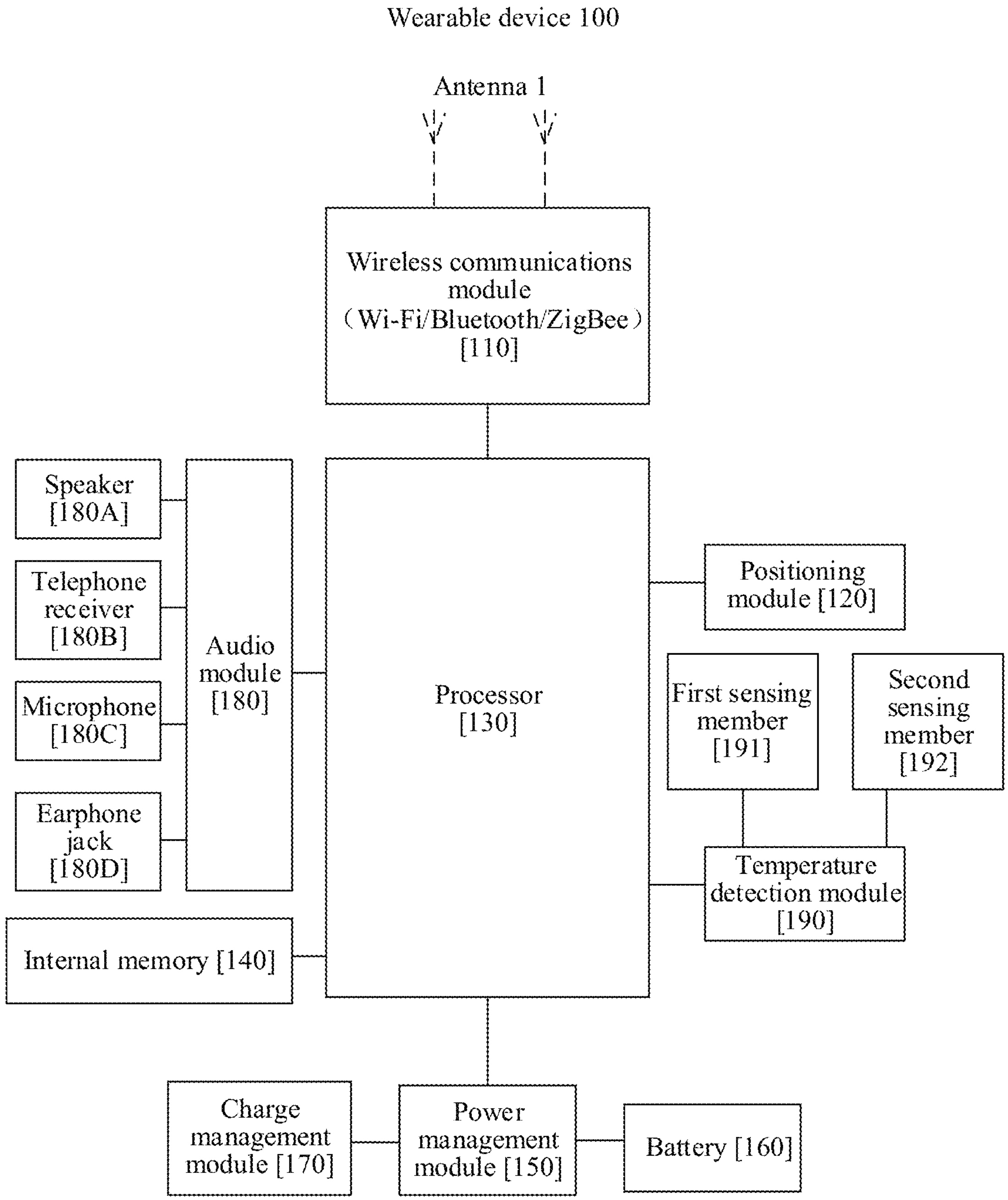
FIG. 1 is a schematic diagram of a hardware structure of a wearable device according to an embodiment of this application.

REFERENCE SIGNS OF MAIN COMPONENTS wearable device 100, 100*a*: first housing 10; opening 11: second housing 20;

earphone handle 30; third housing 40*a*: outer surface 41*a*: inner surface 42*a*; wireless communications module 110;

positioning module 120; processor 130; internal memory 140; power management module 150;

battery 160; charge management module 170; audio module 180; speaker 180A; telephone receiver 180B;

microphone 180C: earphone jack 180D: bone conduction sensor 180E; temperature detection module 190;

first sensing member 191, 191*a*: protrusion 1911: second sensing member 192, 192*a*; accommodating space 193; circuit board 194; via hole 195; connecting member 196;

antenna 1; and electronic device 200; display 210.

This application will be further described with reference to the accompanying drawings in the following specific embodiments.

DESCRIPTION OF EMBODIMENTS

The following clearly and completely describes the technical solutions in the embodiments of this application with reference to the accompanying drawings in the embodiments of this application. It is clear that the described embodiments are only some but not all of the embodiments of this application.

It should be noted that when a component is referred to as being “fastened to” another component, it may be directly fastened to the another component, or there may be a component in between. When a component is deemed as being “connected to” another component, it may be directly connected to the another component, or there may be a component in between. When a component is deemed as being “provided on” another component, it may be directly provided on the another component, or there may be a component in between. The terms “perpendicular”, “horizontal”, “left”, “right”, and other similar expressions as used herein are for illustration only.

In the embodiments of this application, the terms “first”, “second”, and “third” are merely intended for a purpose of description, and shall not be understood as any indication or implication of relative importance or any implicit indication of a quantity of the indicated technical features. Therefore, a feature defined by “first”, “second”, or “third” may explicitly or implicitly include one or more such features.

Unless otherwise specified, data range values recorded in the embodiments of this application should all include end values. Terms used in the embodiments of this application are merely intended to describe specific embodiments rather than to limit this application. As used in the specification of this application and the appended claims, singular expression forms “one”, “a”, “the”, “that”, and “this” are intended to also include, for example, the expression form of “one or more”, unless otherwise expressly specified in the context. It should be further understood that, in the following embodiments of this application, “at least one” and “one or more” mean one or above two (inclusive). The term “and/or” is used for describing an association relationship between associated objects, and indicates that three relationships may be present. For example, A and/or B may indicate the presence of the following three conditions: only A, both A and B, and only B, where A and B may be singular or plural. The character "/" generally indicates an "or" relationship between associated objects.

In addition, reference to "an embodiment", "some embodiments", or the like described in this application means that one or more embodiments of this application include a specific feature, structure, or characteristic described with reference to the embodiment(s). Therefore, expressions such as "in an embodiment", "in some embodiments", "in other embodiments", and "in some other embodiments" appearing in different places in this application do not necessarily refer to the same embodiment(s), but mean "one or more but not all embodiments", unless otherwise specifically emphasized. The terms "include", "comprise", and "have", and variants thereof all mean "including but not limited to", unless otherwise specifically emphasized.

Some embodiments of this application are described in detail. In absence of conflicts, the following embodiments and features in the embodiments may be combined.

Body temperature is one of vital signs of a human body, long-time body temperature monitoring has practical significance for menstrual cycle management, biological rhythm regulation, chronic disease management, and the like. However, measurement accuracy of current contact-type temperature measurement cannot satisfy user requirements, resulting in poor user experience. Especially when a temperature sensor and a biological body do not stay at a stable contact state, an inaccurate temperature measurement result may result.

For a user, a wearable device features long time wearing and close contact with a human body. Therefore, a wearable device in combination with a contact-type temperature sensor can provide relatively accurate body temperature changing without awareness of the user.

For this, some embodiments of this application provide a wearable device 100 having a temperature detection function and capable of providing relatively accurate temperature measurement data.

The following describes a hardware structure of the wearable device 100 involved in the embodiments of this application. As shown in FIG. 1, FIG. 1 is a schematic diagram of a hardware structure of the wearable device 100 according to an embodiment of this application. The wearable device 100 may include a wireless communications module 110, a positioning module 120, a processor 130, an internal memory 140, a power management module 150, a battery 160, a charge management module 170, an audio module 180, a temperature detection module 190, an antenna 1, and the like.

The processor 130 may include one or more processing units. For example, the processor 130 may include an application processor (application processor, AP), a modem processor, a graphics processing unit (graphics processing unit, GPU), an image signal processor (image signal processor, ISP), a controller, a video codec, a digital signal processor (digital signal processor, DSP), a baseband processor, a neural-network processing unit (neural-network processing unit, NPU), and/or the like.

In some embodiments, the processor 130 may include one or more interfaces. The interface may include an I2C interface, an I2S interface, a PCM interface, a UART interface, an MIPI, a GPIO interface, a SIM card interface, a USB interface, and/or the like.

It can be understood that the interface connection relationship between the modules illustrated in this embodiment of this application is merely an example for description, and constitutes no limitation on the structure of the wearable device 100. In some other embodiments of this application, the wearable device 100 may alternatively use an interface connection manner different from that in the foregoing embodiment, or a combination of a plurality of interface connection manners.

The charge management module 170 is configured to receive a charging input from a charger. The charger may be a wireless charger or a wired charger.

The power management module 150 is configured to connect the battery 160, the charge management module 170, and the processor 130. The power management module 150 receives an input from the battery 160 and/or the charge management module 170, and supplies power to the processor 130, the internal memory 140, an external memory interface, the wireless communications module 110, and the like. The power management module 150 may be further configured to monitor parameters such as battery capacity, battery cycle count, and state of health (leakage and impedance) of the battery.

A wireless communication function of the wearable device 100 may be implemented by the antenna 1, the wireless communications module 110, the positioning module 120, and the like.

The positioning module 120 may provide a positioning technology applied to the wearable device 100. The positioning technology may include positioning technologies based on the BeiDou navigation satellite system (beidou navigation satellite system, BDS), the global positioning system (global positioning system, GPS), the global navigation satellite system (global navigation satellite system, GLONASS), the quasi-zenith satellite system (quasi-zenith satellite system, QZSS), satellite based augmentation systems (satellite based augmentation systems, SBAS), and/or the like.

The internal memory 140 may be configured to store one or more computer programs, where the one or more computer programs include instructions.

The audio module 180 includes electronic components such as a speaker 180A, a telephone receiver 180B, a microphone 180C, an earphone jack 180D, and a bone conduction sensor 180E. It can be understood that the wearable device 100 may implement an audio function by using the audio module 180, the speaker 180A, the telephone receiver 180B, the microphone 180C, the earphone jack 180D, the bone conduction sensor 180E, the application processor, and the like, for example, music play and sound recording.

The audio module 180 is configured to convert digital audio information into an analog audio signal for outputting, and also configured to convert an analog audio input into a digital audio signal. The audio module 180 may be further configured to encode and decode audio signals. In some embodiments, the audio module 180 may be provided in the processor 130, or some functional modules of the audio module 180 are provided in the processor 130.

The speaker 180A, also referred to as a "loudspeaker", is configured to convert an audio electrical signal into a sound signal. The wearable device 100 may be used for listening to music or answering a hands-free call via the speaker 180A.

The telephone receiver 180B, also referred to as an "earpiece", is configured to convert an audio electrical signal into a sound signal. When the wearable device 100 is used for answering a call or playing a voice message, the telephone receiver 180B may be placed near a human ear for listening to a voice.

The microphone 180C, also referred to as a "mic" or "mike", is configured to convert a sound signal into an electrical signal. When making a call or sending a voice message, a user may input a sound signal into the microphone 180C by speaking close to the microphone 180C. The wearable device 100 may be provided with at least one microphone 180C. In some other embodiments, the wearable device 100 may be provided with two microphones 180C, to reduce noise in addition to acquiring sound signals. In some other embodiments, the wearable device 100 may alternatively be provided with three, four, or more microphones 180C to acquire sound signals, reduce noise, identify sound sources, implement directional recording, and the like.

The bone conduction sensor 180E is capable of obtaining vibration signals. In some embodiments, the bone conduction sensor may obtain a vibration signal generated when a human voice vibrates a bone. The bone conduction sensor may also contact human pulses to receive a blood pressure beating signal. In some embodiments, the bone conduction sensor may alternatively be provided in an earphone to form a bone conduction earphone. The audio module 180 may parse out a voice signal from the vibration signal obtained by the bone conduction sensor when a human voice vibrates a bone, so as to implement a voice function. The application processor may parse out heart rate information from the blood pressure beating signal obtained by the bone conduction sensor, so as to implement a heart rate detection function.

The temperature detection module 190 may be configured to acquire temperature data. The temperature detection module 190 includes a first sensing member 191 and a second sensing member 192. The first sensing member 191 is configured to form equivalent capacitance with a user when the wearable device 100 is close to epidermis of the user. Therefore, the first sensing member 191 may be configured to obtain a capacitance value of the equivalent capacitance. The second sensing member 192 is a temperature sensor configured to measure temperature of the first sensing member 191.

The wearable device 100 may be further provided with an optical sensor (for example, an infrared temperature measurement sensor), a motion sensor (for example, an acceleration sensor and a gyroscope), a capacitive sensor, and the like.

It can be understood that based on any one or more of the foregoing sensors, the wearable device 100 can perform wear and removal detection to determine whether the wearable device 100 is being worn or removed (taken off).

For example, when the wearable device 100 is provided with an infrared temperature measurement sensor and an acceleration sensor, the infrared temperature measurement sensor may be used to sense changing of temperature within a preset time and the acceleration sensor may be used to determine whether a wear action has taken place within the preset time, and based on the two aspects, the wearable device 100 can determine whether the wearable device 100 is being worn or removed. For another example, when being provided with a capacitive sensor, the wearable device 100 can determine whether the wearable device 100 is being worn or removed, based on capacitance value changing of the capacitive sensor in wearing and removal of the wearable device 100.

It should be understood that when the wearable device 100 is being worn, the wearable device 100 is worn on the user, for example, on an ear or a wrist. When the wearable device 100 is removed, the wearable device 100 may be placed in a battery box, or on a desk, floor, sofa, or the like, which is not limited in this application.

It can be understood that the structure illustrated in this embodiment of this application does not constitute any specific limitation on the wearable device 100. In some other embodiments of this application, the wearable device 100 may include more or fewer components than shown in the figure, or combine some of the components, split some of the components, or arrange the components differently. The components shown in the figure may be implemented in hardware, software, or a combination of software and hardware.

It can be understood that the wearable device 100 involved in the embodiments of this application may include but is not limited to a smart earphone, a smart watch, a smart tracker, smart glasses, a mobile phone, a virtual reality device, a medical device, and other wearable smart devices (for example, a chest belt and an armband). In other words, the wearable device 100 may be a mobile terminal similar to a smart earphone, a smart watch, or the like, or may be some fixed terminals needing to be worn that are similar to a large medical device and the like.

Currently, the wearable device 100 being a smart earphone is used as an example for description of a process of the wearable device 100 measuring body temperature of a user.

Figure 2:
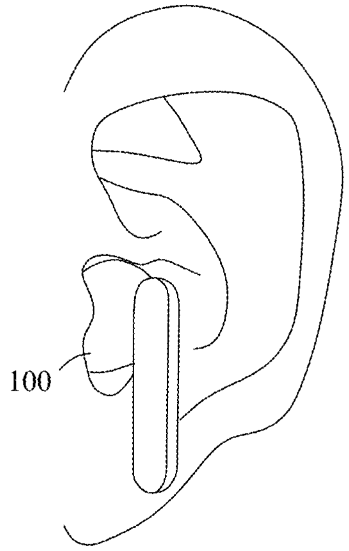
FIG. 2 is a schematic diagram of a wearable device worn on an ear according to an embodiment of this application.
Figure 3:
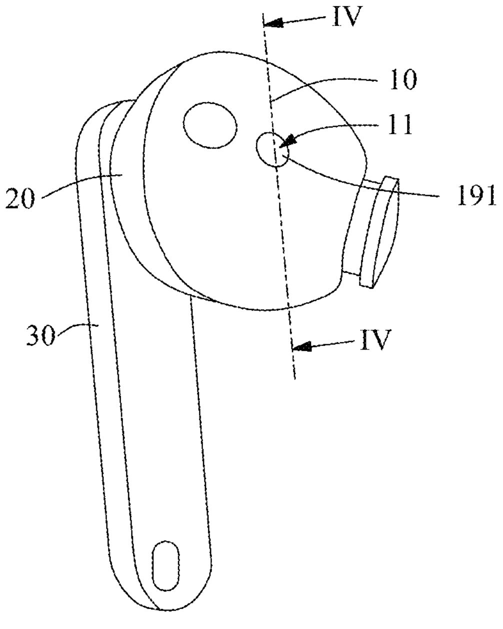
FIG. 3 is a schematic three-dimensional diagram of the wearable device shown in FIG. 2.

Refer to FIG. 2 and FIG. 3 together. The wearable device 100 includes a first housing 10 and a second housing 20. The first housing 10 is a side of the wearable device 100 closer to an ear during use, and the second housing 20 is a side of the wearable device 100 farther away from the ear during use. The first housing 10 is substantially hood-shaped, and an end of the second housing 20 closer to the first housing 10 is also substantially hood-shaped. In this way, the first housing 10 and the second housing 20 are connected to each other to jointly form a substantially spherical accommodating space for accommodating earphone components (for example, the foregoing wireless communications module 110, positioning module 120, processor 130, audio module 180, and temperature detection module 190).

In some embodiments, a side of the second housing 20 farther away from the first housing 10 further extends downward to form an earphone handle 30. The earphone handle 30 is substantially a hollow tube for accommodating other earphone components (for example, the battery 160 and the charge management module 170).

Figure 4:
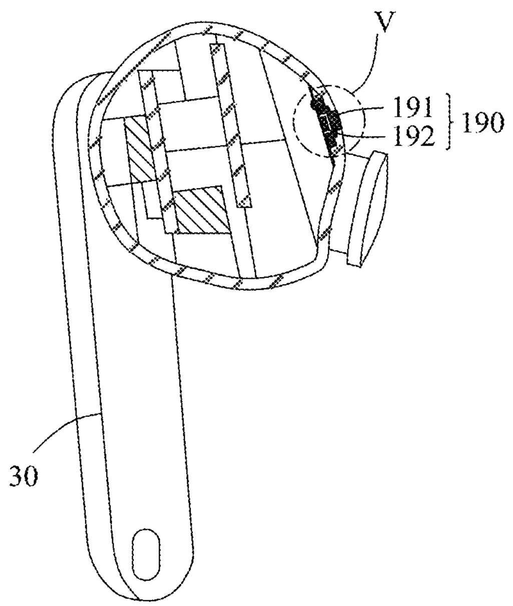
FIG. 4 is a cross-sectional view of the wearable device shown in FIG. 3 along section line IV-IV.

Refer to FIG. 2 to FIG. 4 together. The temperature detection module 190 is disposed close to a surface of the first housing 10. In this way, when the wearable device 100 is worn on the ear of the user, the first housing 10 of the wearable device 100 extends into cavity of auricular concha of the user, so that the temperature detection module 190 contacts skin of the cavity of auricular concha to acquire temperature data of the user.

However, after the user wears the wearable device 100, an action of the user, an external impact, or the like may cause the wearable device 100 to leave the original wear state, so that the temperature detection module 190 changes from a state of contacting to a state of separating from skin of the user, affecting accuracy of the temperature data acquired by the temperature detection module 190.

For this, the wearable device 100 provided in the embodiments of this application may not only acquire the temperature data of the user, but also determine the contact state between the wearable device 100 and the user, so as to determine whether to match a corresponding temperature compensation value to the temperature data acquired by the temperature detection module 190. In this way, accuracy of the temperature data of the user acquired by the wearable device 100 can be further improved.

Figure 5:
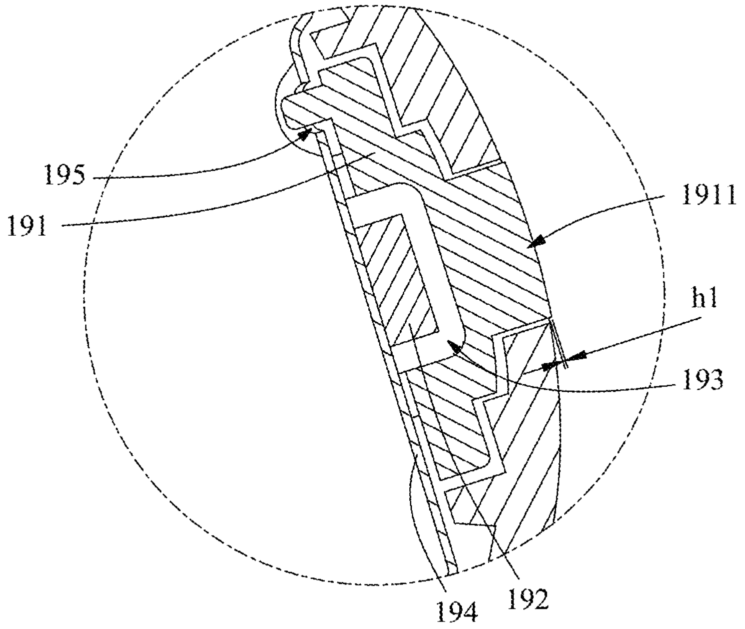
FIG. 5 is a schematic enlarged view of region V in the wearable device shown in FIG. 4.
Figure 6:
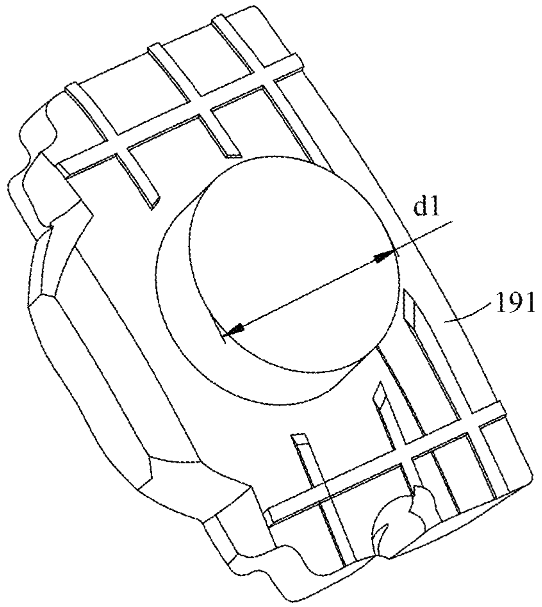
FIG. 6 is a schematic structural diagram of a first sensing member in the wearable device shown in FIG. 4.

Refer to FIG. 4 and FIG. 5 together. In some embodiments, the first sensing member 191 is disposed on a surface of the wearable device 100. In this way, when the wearable device 100 is close to human skin, the first sensing member 191 forms equivalent capacitance with surface of the human body and receives energy transferred or radiated by the human body.

In some embodiments, the first sensing member 191 is made of a material having electric conductivity and thermal conductivity. Thus, in a first aspect, due to a current induction effect of the human body, when the first sensing member 191 is close to the human body, the first sensing member 191 forms equivalent capacitance with the surface of the human body. Further, as the first sensing member 191 approaches the human body, the capacitance value of the equivalent capacitance varies with the distance between the first sensing member 191 and the human body. In a second aspect, when the wearable device 100 is close to or in contact with the human skin, the first sensing member 191 can receive heat of the human body. In this way, after the first sensing member 191 receives heat of the human body for a period of time, the first sensing member 191 reaches a thermal equilibrium state, meaning that temperature of the first sensing member 191 is uniform and substantially equal to temperature of the human body. In this case, the temperature of the first sensing member 191 is acquired through measurement to characterize the temperature of the human body.

The second sensing member 192 is a temperature sensor disposed close to the first sensing member 191 for measuring temperature of the first sensing member 191.

In some embodiments, the first sensing member 191 may be made of a metal material. It can be understood that the metal material having both good electric conductivity and thermal conductivity facilitates fast heat conduction to reach thermal equilibrium, so that the second sensing member 192 quickly acquires the temperature data of the user.

Still refer to FIG. 2 and FIG. 4 to FIG. 6. In some embodiments, the first housing 10 is further provided with an opening 11. The first sensing member 191, substantially hat-shaped, is fitted onto an inner surface of the first housing 10. A protrusion 1911 is formed on an end of the first sensing member 191. The protrusion 1911 is accommodated in the opening 11, and the protrusion 1911 has a first height h1 (at least 0.05 millimeters) with respect to the surface of the first housing 10, so as to better contact the epidermis of the user. The protrusion 1911 is provided in correspondence to the opening 11, and a diameter d1 of the protrusion 1911 is substantially 2.1 mm. In this way, the first sensing member 191 partially protrudes from the surface of the housing 10 via the protrusion 1911. When the wearable device 100 is worn on an ear of the user, the protrusion 1911 of the first sensing member 191 can contact the skin of the user.

A side of the first sensing member 191 farther away from the opening 11 is further provided with an accommodating hole so as to form an accommodating space 193. The accommodating space 193 is configured to accommodate the second sensing member 192. In this way, the second sensing member 192 is disposed on a side of the first sensing member 191 farther away from the epidermis of the user, and the first sensing member 191 covers the second sensing member 192. This helps reduce interference from the external environment, enabling more accurate measurement on the temperature of the first sensing member 191 by the second sensing member 192. An insulating and thermally conductive material (not shown in the figure), for example, an insulating and thermally conductive adhesive, is further filled between the first sensing member 191 and the second sensing member 192, and configured to conduct heat of the first sensing member 191 to the second sensing member 192, making it convenient for the second sensing member 192 to measure temperature.

It can be understood that in some embodiments, the second sensing member 192 may also be fitted onto the first sensing member 191. In this way, the second sensing member 192 can directly contact the first sensing member 191 to measure the temperature of the first sensing member 191, without any insulating and thermally conductive material filled between the first sensing member 191 and the second sensing member 192.

It can be understood that with the first sensing member 191 forming the protrusion 1911 and the protrusion 1911 running through the opening 11 to directly contact the epidermis of the user, interference from the environment to the first sensing member 191 can be effectively reduced, so that the first sensing member 191 quickly reaches the thermal equilibrium state.

It can be understood that in other embodiments, the first sensing member 191 is not limited to the hat shape as in this embodiment, and the shape of the first embodiment may be designed as appropriate to a specific structure of the wearable device, provided that the first sensing member 191 is disposed close to the epidermis of the user and the second sensing member 192 is disposed on the side of the first sensing member 191 farther away from the epidermis of the user. For example, in some embodiments, the first sensing member 191 may alternatively be a substantially sheet-shaped metal, the second sensing member 192 is disposed on the side of the first sensing member 191 farther away from the epidermis of the user, and the second sensing member 192 is fitted onto the first sensing member 191.

It can be understood that in other embodiments, the first sensing member 191 may alternatively be directly disposed on the surface of the wearable device 100 to directly contact the epidermis of the user. It can be understood that a wearable device with a relatively closed temperature measurement environment is preferentially selected for this design, for example, a wearable device with a temperature measurement environment being ear cavity, armpit, hypoglossis, or the like. In this way, interference from the environment to the first sensing member 191 can be reduced.

Still refer to FIG. 5. Both the first sensing member 191 and the second sensing member 192 are disposed on a circuit board 194 (for example, a flexible printed circuit board). In this way, the second sensing member 192 can be accommodated in a closed space jointly formed by the first sensing member 191 and circuit board 194. Thus, heat of the first sensing member 191 can be kept inside the closed space to a large extent, helping improve accuracy of measurement on the first sensing member 191 by the second sensing member 192. Several via holes 195 are also formed on the circuit board 194, so that the first sensing member 191 can extend through the via holes to be connected to the processor 130. The second sensing member 192 may alternatively run through the via hole 195 through a wire to be electrically connected to the processor 130.

It can be understood that the processor 130 is electrically connected to the first sensing member 191 to obtain the capacitance value of the equivalent capacitance formed by the first sensing member 191 with the human body. It can be understood that based on a calculation formula for capacitance, when other conditions are unchanged, a smaller distance between the first sensing member 191 and the human body means a greater capacitance value of the equivalent capacitance formed by the first sensing member 191 with the human body. As such, the processor 130 may determine, based on the obtained capacitance value, a contact state between the first sensing member 191 and the human body, which means the distance between the first sensing member 191 and the human body.

The processor 130 is further electrically connected to the second sensing member 192 to obtain the temperature data obtained by the second sensing member 192 and take the temperature data as an initial temperature. It can be understood that when the first sensing member 191 is in contact with the human body and reaches a thermal equilibrium state, temperature of the first sensing member 191 obtained by the second sensing member 192 can be considered as temperature of the human body. When the first sensing member 191 is spaced from the human body, temperature of the first sensing member 191 obtained by the second sensing member 192 in this case is actually different from temperature of the human body to some extent. As such, according to the contact state between the first sensing member 191 and the epidermis of the user, the processor 130 directly takes the initial temperature as a measured temperature of the user, or matches a corresponding temperature compensation value to the initial temperature and takes a sum of the initial temperature and the temperature compensation value as a measured temperature of the user, so as to improve temperature measurement accuracy.

It can be understood that in some embodiments, the contact state between the first sensing member 191 and the skin of the user may be divided into three states, for example, a touch state, a proximity state, and a hovering state.

Figure 7:
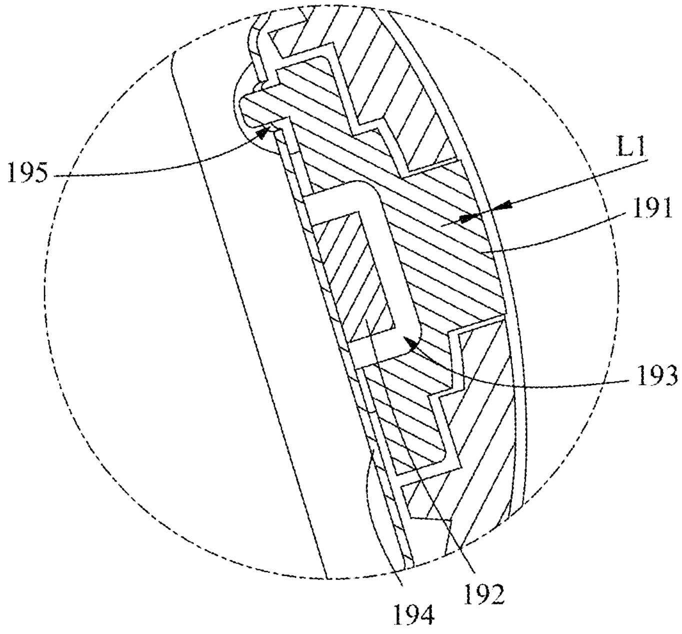
FIG. 7 is a schematic diagram of the wearable device shown in FIG. 4 being in a touch state with epidermis of a user.
Figure 8:
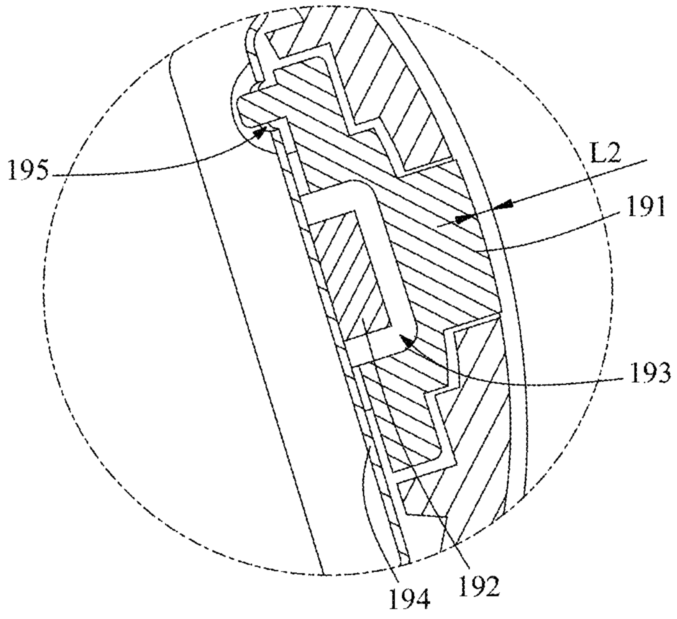
FIG. 8 is a schematic diagram of the wearable device shown in FIG. 4 being in a proximity state with epidermis of a user.
Figure 9:
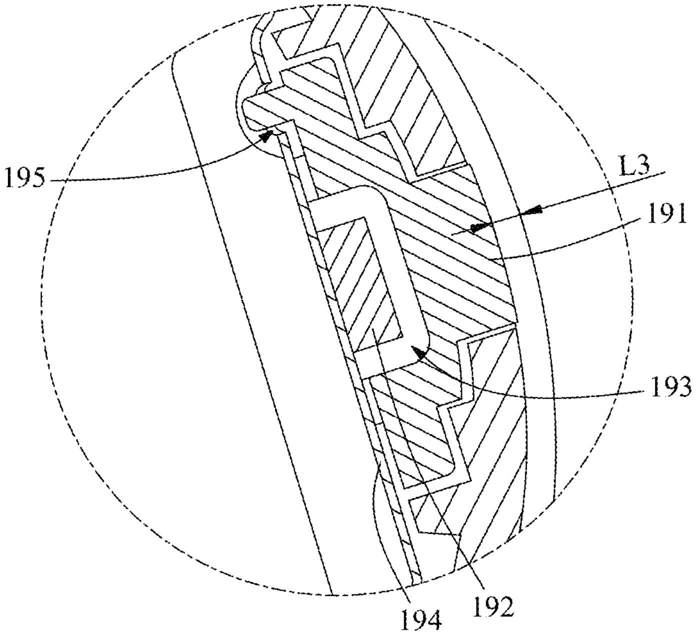
FIG. 9 is a schematic diagram of the wearable device shown in FIG. 4 being in a hovering state with epidermis of a user.

Refer to FIG. 7 to FIG. 9 together. The touch state is a state where the first sensing member 191 is apart from the epidermis of the user by a distance between 0 millimeters and a first distance L1 (for example, 0.05 mm). The proximity state is a state where the first sensing member 191 is spaced from the skin of the user with a distance between the first sensing member 191 and the skin of the user greater than the first distance L1 and less than a second distance L2 (for example, 3 millimeters). The hovering state is a state where the first sensing member 191 is spaced from the user with a distance between the first sensing member 191 and the skin of the user greater than or equal to the second distance L2 (for example, 3 millimeters). The second distance L2 is greater than the first distance L1. For example, the first sensing member 191 shown in FIG. 9 is apart from the epidermis of the user by a third distance L3, where the third distance L3 is greater than the second distance L2. The distance between the first sensing member 191 and the epidermis of the user may be characterized by magnitude changing of the capacitance value. Therefore, the wearable device 100 can be tested so as to obtain capacitance thresholds corresponding to the first sensing member 191 being at the first distance L1 and the second distance L2, so as to determine a contact state between the first sensing member 191 and the user.

For example, in some embodiments, tests are performed on the wearable device 100. When the distance between the first sensing member 191 and the epidermis of the user is the first distance L1, a capacitance value of equivalent capacitance formed by the first sensing member 191 with the epidermis of the user as obtained by the processor 130 is a first capacitance threshold. When the distance between the first sensing member 191 and the epidermis of the user is the second distance L2, a capacitance value of equivalent capacitance formed by the first sensing member 191 with the epidermis of the user as obtained by the processor 130 is a second capacitance threshold.

Thus, when the capacitance value of the equivalent capacitance as obtained by the processor 130 is greater than or equal to the first capacitance threshold, the processor 130 determines that the contact state between the first sensing member 191 and the skin of the user is the touch state. It can be understood that when the processor 130 determines that the wearable device 100 is being worn on an ear of the user through other sensors (for example, the infrared temperature measurement sensor and the acceleration sensor recorded above), and the processor 130 determines that capacitance on the first sensing member 191 is great than or equal to the first capacitance threshold, meaning that the first sensing member 191 is in the touch state with the skin of the user, the processor 130 controls the second sensing member 192 to start temperature measurement, and when the first sensing member 191 reaches a thermal equilibrium state, the processor 130 starts to read a temperature value on the second sensing member 192 as an initial temperature, thus taking the initial temperature read in real time as a real-time measured temperature of the user. In this way, the processor reads the temperature only after the first sensing member 191 reaches the thermal equilibrium state, making the temperature measurement more accurate.

It can be understood that in some embodiments, when the temperature of the first sensing member 191 obtained by the second sensing member 192 is kept in a stable state, for example, temperature fluctuations of the first sensing member 191 are maintained in a given range within a preset time, the first sensing member 191 can be considered to have reached a thermal equilibrium state. It can be understood that a time for the first sensing member 191 to reach the thermal equilibrium state is related to the structure of the first sensing member 191 and a heat conduction path between the first sensing member 191 and the human body. The preset time and the temperature fluctuation range are not limited in this application.

It can be understood that when the processor 130 determines that the wearable device 100 is still worn on the ear of the user, and the capacitance on the first sensing member 191 as obtained by the processor 130 is great than or equal to the second capacitance threshold and less than the first capacitance threshold, the processor 130 determines that the contact state between the first sensing member 191 and the user is the proximity state. As such, the first sensing member 191 is not in close contact with the skin of the user, and heat of the first sensing member 191 conducted to the second sensing member 192 through the insulating and thermally conductive material cannot represent the current true body temperature of the user. Therefore, when the processor 130 determines that the contact state between the first sensing member 191 and the skin of the user is the proximity state, the processor 130 further matches a temperature compensation value to the initial temperature read by the second sensing member 192 and takes a sum of the temperature compensation value and the initial temperature as a measured temperature of the user.

In other words, when the processor 130 detects that the contact state between the first sensing member 191 and the human body is the proximity state, the measured temperature of the human body satisfies the following formula:

$$T=T_1+T_{com}, \text{ where}$$

$T_1$ represents the initial temperature read by the second sensing member 192 and $T_{com}$ represents the corresponding temperature compensation value.

It can be understood that in the embodiments of this application, the temperature of the user is determined by the first sensing member 191 touching or approaching the epidermis of the user to absorb heat and then the second sensing member 192 measuring the temperature of the first sensing member 191. It is clear that when the first sensing member 191 is closer to the epidermis of the user, the temperature obtained by the second sensing member 192 can characterize the temperature of the user more accurately, and the needed temperature compensation value is smaller. In other words, when the contact state between the first sensing member 191 and the user is the proximity state, the distance between the first sensing member 191 and the epidermis of the user is positively correlated with the temperature compensation value. In addition, the distance between the first sensing member 191 and the epidermis of the user is negatively correlated with the capacitance value of the equivalent capacitance (as learned from the calculation formula for capacitance). Therefore, when the contact state between the first sensing member 191 and the human body is the proximity state, the capacitance value of the equivalent capacitance is negatively correlated with the temperature compensation value. In other words, when the contact state between the first sensing member 191 and the human body is the proximity state, the capacitance value of the equivalent capacitance is greater and the temperature compensation value is smaller. It can be understood that in some embodiments, several groups of tests may be used to obtain capacitance values, initial temperature values, and actual temperature values corresponding to the first sensing member 191 being at different distances to the epidermis of the user, when the contact state between the first sensing member 191 and the epidermis of the user is the proximity state. It can be understood that a difference between the actual temperature value and the initial temperature value is an ideal temperature compensation value. By fitting the capacitance values and the ideal temperature compensation values in data of the foregoing several groups of tests, a function between the capacitance value and the temperature compensation value can be established which is stored in the internal memory 140. As such, the processor 130 calls the function in the internal memory 140 and the obtained capacitance value of the equivalent capacitance to calculate a corresponding temperature compensation value.

It can be understood that in some embodiments, when the processor 130 detects that the first sensing member 191 is in the proximity state with the epidermis of the user, the processor 130 may further subdivide the proximity state into several states based on different capacitance values, for example, a first proximity state and a second proximity state. In this way, finer temperature compensation can be further performed on the initial temperature in the proximity state, so as to improve accuracy of the temperature measurement data.

When the processor 130 determines that the wearable device 100 is still worn on the ear of the user, and the capacitance on the first sensing member 191 as obtained by the processor 130 is less than the second capacitance threshold, the processor 130 determines that the contact state between the first sensing member 191 and the user is the hovering state. In this case, the temperature data currently acquired by the second sensing member 192 can be considered to be unreliable, and alert information is output to the user, for example, alerting the user to tighten the wearable device 100. When the first sensing member 191 is detected to be in the touch state or the proximity state with the user, the body temperature data of the user is acquired again according to the foregoing control process.

In some embodiments, the wearable device 100 further includes an alert module. For example, the alert module may be the audio module 180. In this way, when the processor 130 determines that the first sensing member 191 is in the hovering state with the epidermis of the user, the processor 130 controls the audio module 180 to output corresponding audio information, to alert the user to tighten the wearable device 100.

It can be understood that when the processor 130 determines that the wearable device 100 is taken off, the operation of detecting the contact state between the first sensing member 191 and the skin of the user is not performed.

In some embodiments, the wearable device 100 further includes an analog to digital converter (Analog to Digital Converter, ADC). The first sensing member 191 is connected to the ADC through a general-purpose input/output (General-purpose input/output, GPIO) interface. The ADC is further electrically connected to the processor 130. The ADC is configured to convert the capacitance value of the equivalent capacitance formed by the first sensing member 191 with the epidermis of the user into a digital quantity (referred to as ADC value below), and output the digital quantity to the processor 130. It can be understood that the capacitance value of the equivalent capacitance is related to the distance between the first sensing member 191 and the epidermis of the user. Therefore, the ADC value is related to the distance between the first sensing member 191 and the epidermis of the user. In other words, as the distance between the first sensing member 191 and the epidermis of the user changes, the ADC value corresponding to the first sensing member 191 as output by the ADC after conversion also changes synchronously.

For example, in some embodiments, data shown in the table below is detected:

| Distance between first sensing member and epidermis of human body | ADC value | ADC value variation as compared with hovering state | Temperature |
|---|---|---|---|
| 0 millimeters | 5300 | 1500 | 35.2° C. |
| 0.5 millimeters | 6690 | 110 | 34.7° C. |
| 1 millimeter | 6700 | 100 | 34.5° C. |
| 3 millimeters | 6800 | / | 27.375° C. |

According to the foregoing table, for example, when the distance between the first sensing member 191 and the epidermis of the human body is 0 millimeters, meaning that the contact state between the first sensing member 191 and the epidermis of the human body is the touch state, the corresponding ADC value is 5300. When the distance between the first sensing member 191 and the epidermis of the human body is 3 millimeters, meaning that the contact state between the first sensing member 191 and the epidermis of the human body is the hovering state, the corresponding ADC value is 6800, and the ADC values in the touch state and the hovering state have a difference of 1500, generating an obvious jump. Similarly, when the distance between the first sensing member 191 and the epidermis of the human body is 0.5 millimeters, meaning that the contact state between the first sensing member 191 and the epidermis of the human body is the proximity state, the corresponding ADC value is 6690. The ADC values in the proximity state and the hovering state have a difference of 110, also generating an obvious jump. It is clear that with small changes in the distance between the first sensing member 191 and the epidermis of the human body, the ADC value corresponding to the first sensing member 191 has jumps of large values. Therefore, the ADC value can effectively represent the small changes in the distance between the first sensing member 191 and the epidermis of the human body, helping improve temperature measurement accuracy.

In some embodiments, changes of the ADC value can be used to directly characterize changes of the capacitance on the first sensing member 191, which in turn characterize the changes in the distance between the first sensing member 191 and the epidermis of the user.

It can be understood that an ADC value-capacitance function may vary depending on the model of the ADC. For example, in some embodiments, when an ADC of a given model is used, the ADC value-capacitance function is $$c = \frac{4096 - \left(\frac{a}{4}\right)}{\frac{a}{4}} * 15$$

It can be understood that in the foregoing function, c is the capacitance value of the equivalent capacitance formed by the first sensing member 191 with the human body as obtained by the processor 130, and a is the ADC value. According to the foregoing function, the ADC value a is negatively correlated with the capacitance value c. Thus, for determining of the processor 130 on the contact state between the first sensing member 191 and the human body based on the ADC value, the processor 130 may also perform the determining based on a corresponding ADC threshold.

For example, in some embodiments, tests are performed on the wearable device 100. When the distance between the first sensing member 191 and the epidermis of the user is the first distance L1, an ADC value obtained by the processor 130 is a first ADC threshold. When the distance between the first sensing member 191 and the epidermis of the user is the second distance L2, an ADC value obtained by the processor 130 is a second ADC threshold. The first ADC threshold is less than the second ADC threshold.

In some embodiments, when detecting that the ADC value corresponding to the first sensing member 191 is less than or equal to the first ADC threshold (for example, 5500), the processor 130 determines that the first sensing member 191 is in the touch state with the skin of the user. Therefore, the processor 130 determines that the temperature data acquired by the second sensing member 192 can be taken as the body temperature data of the user, without matching a corresponding temperature compensation value.

In some embodiments, when detecting that the ADC value corresponding to the first sensing member 191 is greater than the first ADC threshold (for example, 5500) and less than or equal to the second ADC threshold (for example, 6750), the processor 130 determines that the first sensing member 191 is in the proximity state with the skin of the user. Therefore, the processor 130 determines to match a corresponding temperature compensation value to the temperature data acquired by the second sensing member 192, so as to take the temperature data acquired by the second sensing member 192 and the temperature compensation value together as the body temperature data of the user.

It can be understood that the temperature compensation value is related to the distance between the first sensing member 191 and the epidermis of the user. As can be learned from the foregoing content, the distance between the first sensing member 191 and the epidermis of the user can be characterized by the capacitance value, and the capacitance value can be characterized by the ADC value. Therefore, the temperature compensation value can also be characterized by the ADC value. As such, in some embodiments, several groups of tests may be used to obtain ADC values, initial temperature values, and actual temperature values corresponding to the first sensing member 191 being at different distances to the epidermis of the user, when the contact state between the first sensing member 191 and the epidermis of the user is the proximity state. It can be understood that a difference between the actual temperature value and the initial temperature value is an ideal temperature compensation value. By fitting the ADC values and the ideal temperature compensation values in data of the foregoing several groups of tests, a function between the ADC value corresponding to the first sensing member 191 and the temperature compensation value can be established which is stored in the internal memory 140. The processor 130 calls the function in the internal memory 140 and the obtained ADC value corresponding to the first sensing member 191 so as to calculate a corresponding temperature compensation value.

It can be understood that the calculation function of the temperature compensation value may vary with the structure of the first sensing member 191 and the environment. The calculation function of the temperature compensation value is not limited in this application. For example, in some embodiments, fitting is performed on the basis that the wearable device 100 is worn in the cavity of auricular concha and that the wearable device 100 is provided with the first sensing member 191 shown in FIG. 6, to obtain a relationship between the temperature compensation value and the ADC value that satisfies the following formula:

$$T_{com} = -0.00004(a-5500)^2 + 0.0995(a-5500) - 61.303,$$

where $T_{com}$ represents the temperature compensation value and a represents the ADC value corresponding to the first sensing member 191.

Therefore, when the first sensing member 191 is in the proximity state with the user, the body temperature data of the user is $$T = T_1 + T_{com},$$ where T is a final measured temperature, $T_1$ is the initial temperature acquired by the second sensing member 192, and $T_{com}$ is the calculated temperature compensation value.

In some embodiments, when detecting that the ADC value corresponding to the first sensing member 191 is greater than the second ADC threshold (for example, 6750), the processor 130 determines that the first sensing member 191 is in the hovering state with the skin of the user, and the processor 130 determines that the currently acquired initial temperature is unreliable, and controls the alert module to output corresponding alert information, to alert the user to tighten the wearable device 100.

It can be understood that when the user is moving (for example, walking or running) wearing the wearable device 100, the wearable device 100 may switch between the touch state and the proximity state multiple times in a short time due to actions of the user. As such, the measured temperature of the user may be inaccurate. To improve accuracy of the measured temperature of the wearable device 100, in some embodiments, the processor 130 may further obtain a plurality of temperatures measured within a preset period (for example, ten seconds), and take an average value of the plurality of temperatures measured within the preset period as a final measured temperature which is reported to the user. In this way, errors caused by the switching between contact states can be effectively reduced.

Figure 10:
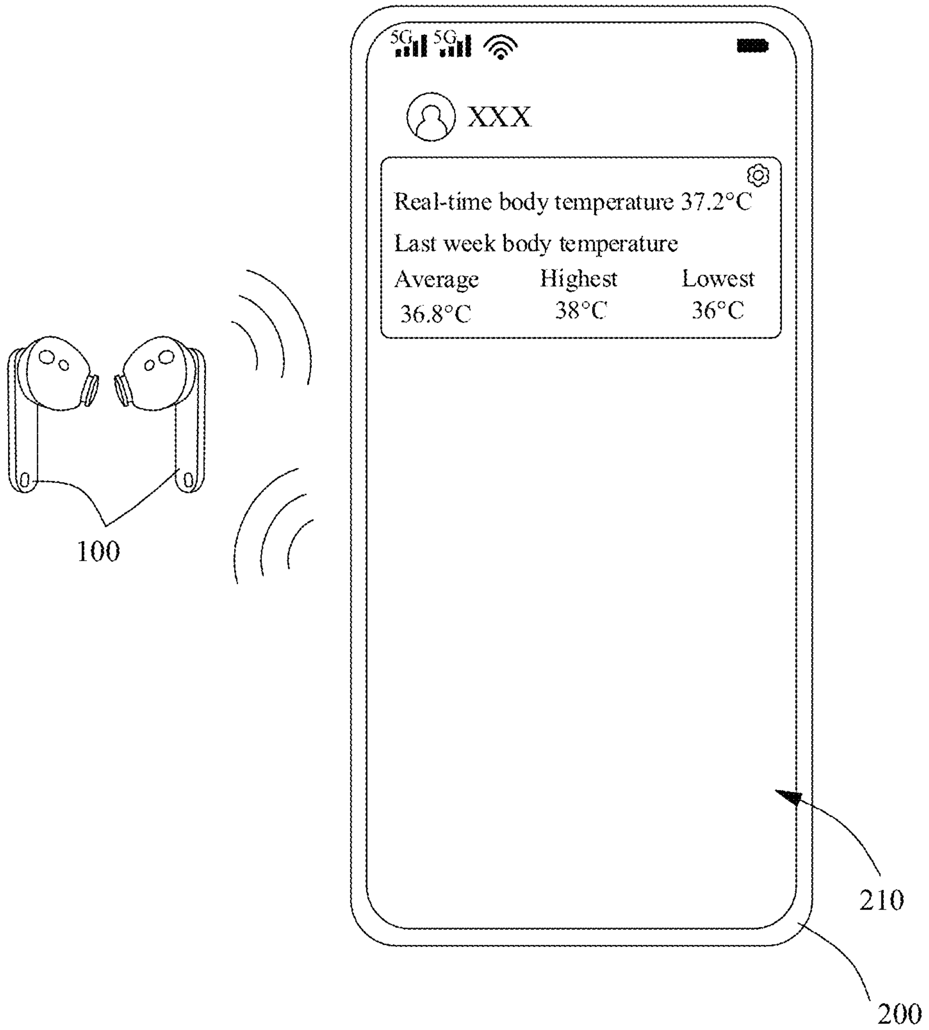
FIG. 10 is a schematic diagram of a temperature measurement scenario of the wearable device shown in FIG. 2.

Still refer to FIG. 10. FIG. 10 is a schematic diagram of a temperature measurement scenario of the wearable device 100 according to an embodiment of this application. It can be understood that the wearable device 100 may be connected to an electronic device 200 through Bluetooth, Wi-Fi, near field communications, or other manners, and the wearable device 100 can transmit the finally obtained measured temperature data to the electronic device 200. Thus, when starting a given application, a user can view the body temperature on a corresponding display screen of the application.

It can be understood that the electronic device 200 includes a display 210. In some embodiments, compared with the wearable device 100, the electronic device 200 can display more data in addition to the body temperature data of the user. For example, the display 210 can display real-time body temperature of the user, and average body temperature, highest body temperature, and lowest body temperature of the user in the last week. In some embodiments, when the processor 130 detects that the first sensing member 191 is in the hovering state with the epidermis of the user, the processor 130 can perform further control so as to output alert information to the electronic device 200, where the alert information is displayed on the display 210 of the electronic device 200 to alert the user to tighten the wearable device for ease of temperature measurement.

It can be understood that in some embodiments, while measuring the temperature, the wearable device 100 may further periodically play the obtained temperature in voice to the user via the audio module 180.

It can be understood that in some embodiments, the user wears two wearable devices 100 at the same time for respective temperature measurement through left and right ears. The two wearable devices 100 may communicate through Bluetooth, near field communications, or Wi-Fi, so as to transmit temperature data obtained by one wearable device 100 to the other wearable device 100. Thus, a measured temperature finally reported to the user is an average temperature of temperatures measured by the two wearable devices 100, which further improves accuracy of temperature measurement by the wearable device 100.

In some embodiments, when the user wears two wearable devices 100 at the same time, one of the wearable devices 100 may be used as a primary device and the other wearable device 100 may be used as a secondary device, and temperature measurement is first performed by the wearable device 100 that is used as the primary device. When the wearable device 100 that is used as the primary device runs out of power or is taken off, the wearable device 100 that is used as the secondary device takes over to perform temperature measurement. In this way, the power of the two wearable devices 100 can be effectively saved, prolonging endurance life of the two wearable devices 100.

It can be understood that in some embodiments, the processor 130 of the wearable device 100 may enable a temperature measurement function after detecting that a user has performed a corresponding operation. For example, in some embodiments, the wearable device 100 further includes an acceleration sensor. During operation of the wearable device 100, the processor 130 may start or stop reading the temperature of the second sensing member 192 according to a tap operation (for example, tapping, double-tapping, and triple-tapping) detected by the acceleration sensor, so as to enable or disable the temperature measurement function of the wearable device 100. After the user enables the temperature measurement function of the wearable device 100, the processor 130 further needs to determine according to the foregoing control process whether the contact state between the first sensing member 191 and the epidermis of the user is the touch state. When the processor 130 determines that the contact state between the first sensing member 191 and the epidermis of the user is not the touch state, the processor 130 controls the alert module to send alert information, so that the first sensing member 191 and the epidermis of the user reach the touch state, after which the processor 130 controls the second sensing member 192 to start temperature measurement.

It can be understood that the foregoing specific values of the first distance L1, the second distance L2, the first ADC threshold, and the second ADC threshold are merely used as examples for description. The first distance L1, the second distance L2, the first capacitance threshold, the second capacitance threshold, the first ADC threshold, and the second ADC threshold are not specifically limited in the embodiments of this application.

It can be understood that the wearable device 100 provided in the embodiments of this application is not limited to measuring temperature of humans. In some scenarios, the wearable device 100 provided in the embodiments of this application or a wearable device improved based on the inventive idea of this application can also be used to measure temperature of other biological bodies, for example, measuring temperature of pet dogs or pet cats.

Figure 11:
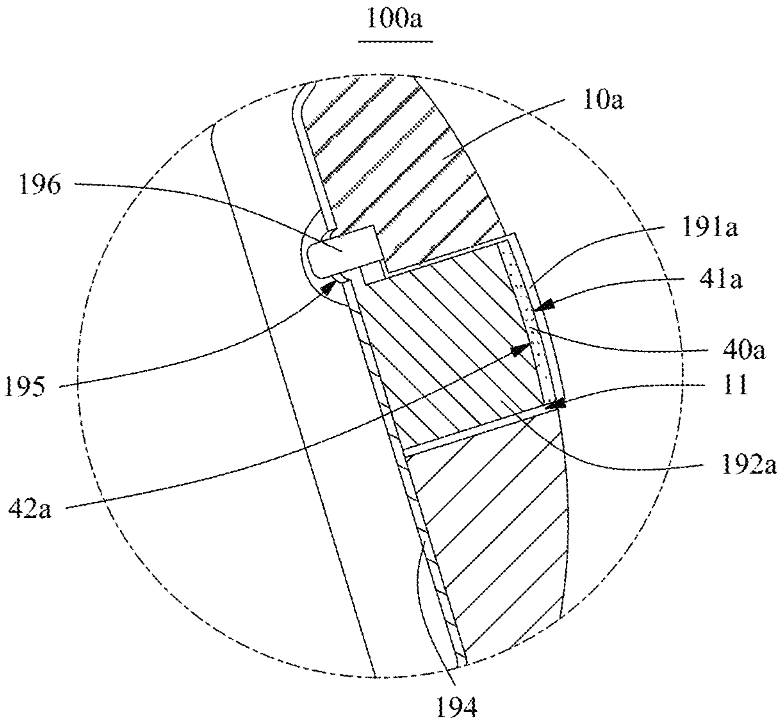
FIG. 11 is a partial cross-sectional view of a wearable device according to another embodiment of this application.

Still refer to FIG. 11. An embodiment of this application further provides a wearable device 100*a*. The wearable device 100*a* also includes a first housing 10, a first sensing member 191*a*, a second sensing member 192*a*, and a processor 130 (not shown in the figure). The wearable device 100*a* has substantially the same structure as the wearable device 100, except that arrangement of the first sensing member 191*a* and the second sensing member 192*a* in the wearable device 100*a* is different from arrangement of the first sensing member 191 and the second sensing member 192 in the wearable device 100, and that the wearable device 100*a* further includes a third housing 40*a*.

In some embodiments, the first housing 10 of the wearable device 100*a* is also provided with an opening 11. The opening 11 is covered with the third housing 40*a*. The third housing 40*a* includes an outer surface 41*a* and an inner surface 42*a*. The second sensing member 192*a* is accommodated in the opening 11. The second sensing member 192*a* is fitted onto the inner surface 42*a*. The first sensing member 191*a* is disposed on the outer surface 41*a*. The first sensing member 191*a* extends along a side of the second sensing member 192*a* to a via hole 195 in a circuit board 194, to be electrically connected to the processor 130 through a connecting member 196 (for example, an elastic metal sheet) at the via hole 195.

In some embodiments, the first sensing member 191*a* is a material layer, having electric conductivity and thermal conductivity, covering the outer surface 41*a* of the third housing 40*a*, for example, a metal thin film. The second sensing member 192*a* is a temperature sensor. The third housing 40*a* is made of an insulating and thermally conductive material, for example, glass. It can be understood that the first sensing member 191*a* is close to or in contact with epidermis of a user to form equivalent capacitance with the epidermis of the user and absorb heat of the user. Then the first sensing member 191*a* conducts the heat to the third housing 40*a*. In this way, the second sensing member 192*a* can obtain temperature of the first sensing member 191*a* by measuring temperature of the third housing 40*a*.

It can be understood that a process of the wearable device 100*a* determining a contact state between the first sensing member 191*a* and the user by obtaining capacitance on the first sensing member 191*a* is the same as the determining method of the wearable device 100, and details are not described herein again.

An embodiment of this application further provides a temperature measurement method applied to a wearable device. The wearable device includes a first sensing member and a second sensing member. The first sensing member has a capacitance value. The second sensing member is configured to measure temperature of the first sensing member as an initial temperature. The temperature measurement method includes:

Step S1: Obtain the capacitance value of the first sensing member to determine a contact state of the wearable device.

Step S2: According to the contact state, directly take the initial temperature as a measured temperature, or match a corresponding temperature compensation value to the initial temperature and take a sum of the initial temperature and the temperature compensation value as a measured temperature.

In step S2, when the capacitance value is greater than or equal to a first capacitance threshold, the contact state is determined to be a touch state, and the initial temperature is taken as the measured temperature.

When the capacitance value is less than the first capacitance threshold and greater than or equal to a second capacitance threshold, the contact state is determined to be a proximity state, the corresponding temperature compensation value is matched to the initial temperature, and the sum of the initial temperature and the temperature compensation value is taken as the measured temperature.

When the capacitance value is less than the second capacitance threshold, the contact state is determined to be a hovering state.

In some embodiments, the wearable device further includes an alert module, and when the contact state is determined to be the hovering state, controls the alert module to output alert information.

In some embodiments, the wearable device further includes an analog to digital converter. The analog to digital converter has one end connected to the first sensing member and another end connected to a processor. The analog to digital converter is configured to convert the capacitance value of equivalent capacitance into a digital quantity. A functional relationship between the temperature compensation value and the digital quantity is:

$$T_{com}=-0.00004(a-5500)^2+0.0995(a-5500)-61.303,$$

where $T_{com}$ represents the temperature compensation value and a represents the digital quantity.

It can be understood that the foregoing technical solutions are not limited to application in earphones. In other embodiments, the foregoing technical solutions can also be implemented in other wearable devices such as smart watches and activity trackers.

It can be understood that the foregoing embodiments are merely intended to describe the technical solutions of this application, but not intended to constitute any limitation. Although this application is described in detail with reference to the foregoing preferred embodiments, persons of ordinary skill in the art should understand that modifications or equivalent replacements can be made to the technical solutions of this application, without departing from the spirit and scope of the technical solutions of this application.

What is claimed is:

1. A wearable device, wherein the wearable device comprises:

a first sensing member comprising a material having electric conductivity and thermal conductivity, the first sensing member configured to obtain a capacitance value of a capacitance formed by the first sensing member with an epidermis of a user;

an analog to digital converter to convert the capacitance value into a digital quantity;

a second sensing member, configured to measure temperature of the first sensing member as an initial temperature, wherein the second sensing member is disposed on a side of the first sensing member farther away from the epidermis of the user; and a processor, electrically connected to the first sensing member, wherein the processor is configured to read the capacitance value based on the digital quantity and determine a contact state of the wearable device according to the capacitance value; and the processor is further electrically connected to the second sensing member, and configured to read the initial temperature and, according to the contact state, directly take the initial temperature as a measured temperature, or match a corresponding temperature compensation value to the initial temperature based on the capacitance value and take a sum of the initial temperature and the temperature compensation value as a measured temperature, wherein the wearable device comprises a housing, the housing comprises an outer surface and an inner surface, the outer surface is provided with the first sensing member, and the inner surface is provided with the second sensing member, wherein heat of the first sensing member is conducted to the housing, and the second sensing member obtains the temperature of the first sensing member by measuring temperature of the housing.

2. The wearable device according to claim 1, wherein the housing is provided with an opening, and the first sensing member is partly accommodated in the opening so that the first sensing member protrudes from a surface of the housing through the opening.

3. The wearable device according to claim 1, wherein the second sensing member is fitted onto the first sensing member.

4. The wearable device according to claim 1, wherein the first sensing member covers the second sensing member, and an insulating and thermally conductive material is filled between the first sensing member and the second sensing member.

5. The wearable device according to claim 4, wherein the first sensing member is provided with an accommodating hole, and the second sensing member is accommodated in the accommodating hole.

6. The wearable device according to claim 1, wherein the material of the first sensing member is made of metal, and the second sensing member is a temperature sensor.

7. The wearable device according to claim 1, wherein when the capacitance value is greater than or equal to a first capacitance threshold, the contact state is determined to be a touch state, and the initial temperature is taken as the measured temperature.

8. The wearable device according to claim 7, wherein when the contact state is the touch state, the second sensing member is controlled to start temperature measurement and read the initial temperature when the first sensing member reaches a thermal equilibrium state after a preset time.

9. The wearable device according to claim 8, wherein when the capacitance value is less than the first capacitance threshold and greater than or equal to a second capacitance threshold, the contact state is determined to be a proximity state, the corresponding temperature compensation value is matched to the initial temperature, and the sum of the initial temperature and the temperature compensation value is taken as the measured temperature.

10. The wearable device according to claim 9, wherein a relationship between the temperature compensation value and the capacitance value satisfies a preset function, and the temperature compensation value is calculated based on the preset function and the obtained capacitance value, wherein the capacitance value is negatively correlated with the temperature compensation value.

11. The wearable device according to claim 9, wherein when the capacitance value is less than the second capacitance threshold, the contact state is determined to be a hovering state; and the wearable device further comprises an alert module, and when the contact state is the hovering state, the alert module outputs alert information.

12. The wearable device according to claim 1, wherein the analog to digital converter has one end connected to the first sensing member and another end connected to the processor, and the analog to digital converter is configured to convert the capacitance value into the digital quantity and output the digital quantity to the processor.

13. The wearable device according to claim 12, wherein a functional relationship between the temperature compensation value and the digital quantity is:

$$T_{com}=-0.00004(a-5500)^2+0.0995(a-5500)-61.303,$$

where $T_{com}$ represents the temperature compensation value and a represents the digital quantity.

14. The wearable device of claim 1, wherein the material layer comprises a metal thin film.

15. A temperature measurement method, comprising:

converting, with an analog to digital converter, a capacitance value of a capacitance formed by a first sensing member with an epidermis of a user to a digital quantity, the first sensing member included in a wearable device, the wearable device comprising a housing including an outer surface and an inner surface, the outer surface provided with the first sensing member, and the first sensing member comprising a material having electric conductivity and thermal conductivity;

measuring, as an initial temperature, a temperature of the first sensing member with a second sensing member included in the wearable device, wherein the inner surface of the housing is provided with the second sensing member and heat of the first sensing member is conducted to the housing, and the second sensing member obtains the temperature of the first sensing member by measuring temperature of the housing;

reading, based on the digital quantity, the capacitance value of the first sensing member to determine a contact state of the wearable device; and according to the contact state, taking the initial temperature as a measured temperature, or matching a corresponding temperature compensation value to the initial temperature based on the capacitance value and taking a sum of the initial temperature and the temperature compensation value as a measured temperature.

16. The temperature measurement method according to claim 15, wherein when the capacitance value is greater than or equal to a first capacitance threshold, the contact state is determined to be a touch state, and the initial temperature is taken as the measured temperature.

17. The temperature measurement method according to claim 16, wherein when the capacitance value is less than the first capacitance threshold and greater than or equal to a second capacitance threshold, the contact state is determined to be a proximity state, the corresponding temperature compensation value is matched to the initial temperature, and the sum of the initial temperature and the temperature compensation value is taken as the measured temperature.

18. The temperature measurement method according to claim 17, wherein when the capacitance value is less than the second capacitance threshold, the contact state is determined to be a hovering state, and wherein the wearable device further comprises an alert module, and when the contact state is determined to be the hovering state, controls the alert module to output alert information.

19. The temperature measurement method according to claim 15, wherein the wearable device further comprises the analog to digital converter, the analog to digital converter has one end connected to the first sensing member and another end connected to a processor, and the analog to digital converter is configured to convert the capacitance value into a digital quantity, wherein a functional relationship between the temperature compensation value and the digital quantity is:

$$T_{com}=-0.00004(a-5500)^2+0.0995(a-5500)-61.303,$$

where $T_{com}$ represents the temperature compensation value and a represents the digital quantity.

20. The temperature measurement method according to claim 16, wherein when the contact state is the touch state, the second sensing member is controlled to start temperature measurement and read the initial temperature when the first sensing member reaches a thermal equilibrium state after a preset time.

* * * * *